United States Patent
Baba et al.

(10) Patent No.: US 11,958,801 B2
(45) Date of Patent: *Apr. 16, 2024

(54) PROCESS FOR PREPARING 6-ISOPROPENYL-3-METHYL-9-DECENYL ACETATE AND INTERMEDIATES THEREOF

(71) Applicant: Shin-Etsu Chemical Co., Ltd., Tokyo (JP)

(72) Inventors: Akihiro Baba, Niigata (JP); Takeshi Kinsho, Niigata (JP); Yusuke Nagae, Niigata (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/154,068

(22) Filed: Jan. 13, 2023

(65) Prior Publication Data

US 2023/0148099 A1 May 11, 2023

Related U.S. Application Data

(62) Division of application No. 17/234,879, filed on Apr. 20, 2021, now Pat. No. 11,591,282.

(30) Foreign Application Priority Data

Apr. 21, 2020 (JP) .................. 2020-075345

(51) Int. Cl.
C07C 67/08 (2006.01)
C07C 69/145 (2006.01)

(52) U.S. Cl.
CPC ............ *C07C 67/08* (2013.01); *C07C 69/145* (2013.01)

(58) Field of Classification Search
CPC ... C07C 67/08; C07C 69/145; C07C 17/2632; C07C 21/19; C07C 29/40; C07C 33/02;
(Continued)

(56) References Cited

U.S. PATENT DOCUMENTS 4,518,813 A * 5/1985 Ernst .................. C07C 17/2632
570/252
2015/0119597 A1 4/2015 Kinsho et al.
(Continued)

FOREIGN PATENT DOCUMENTS

| CN | 109956850 A | 7/2019 |
|---|---|---|
| EP | 2868651 A1 | 5/2015 |
| JP | 2015110553 A | 6/2015 |

OTHER PUBLICATIONS

Baudouy et al., "Synthese diastereoselective d'une composante de la pheromone sexuelle de "l'ecaille rouge de californie" : l'acetate d'isopropenyl-6 methyl-3 decene-9 yle (3S, 6R)", Tetrahedron 44(2), 471-480 Published 1988) (Year: 1988).*

(Continued)

*Primary Examiner* — Jafar F Parsa
*Assistant Examiner* — Blaine G Doletski
(74) *Attorney, Agent, or Firm* — Myers Bigel, P.A.

(57) ABSTRACT

A process for process for preparing 6-isopropenyl-3-methyl-9-decenyl acetate of the following formula (3), wherein Ac represents an acetyl group, the process comprising steps of: preparing a nucleophilic reagent, 5-isopropenyl-2-methyl-8-nonenyl compound, of the following general formula (1): wherein $M^1$ represents Li, $MgZ^1$, $ZnZ^1$, Cu, $CuZ^1$, or $CuLiZ^1$, wherein $Z^1$ represents a halogen atom or a 5-isopropenyl-2-methyl-8-nonenyl group, from a 5-isopropenyl-2-methyl-8-nonenyl halide compound of the following general formula (4): wherein $X^1$ represents a halogen atom; subjecting the nucleophilic reagent (1), 5-isopropenyl-2-methyl-8-nonenyl compound, to an addition reaction with at least one electrophilic reagent selected from the group consisting of formaldehyde, paraformaldehyde, and 1,3,5-trioxane, followed by a hydrolysis reaction to form 6-isopropenyl-3-methyl-9-decenol of the following formula (2); and acetylating 6-isopropenyl-3-methyl-9-decenol (2) to form 6-isopropenyl-3-methyl-9-decenyl acetate (3).

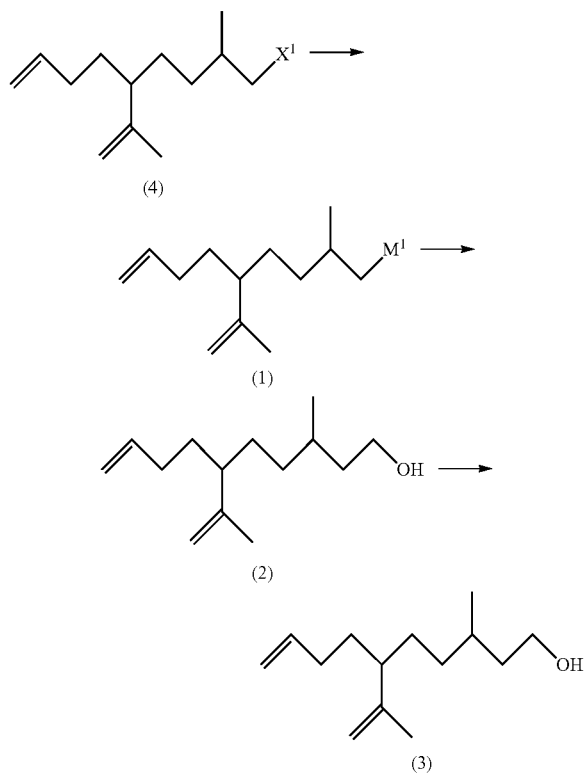

1 Claim, No Drawings

(58) Field of Classification Search
CPC .... G03F 7/0002; G03F 7/705; G03F 7/70725; G03F 7/709; G03F 9/7088; G05B 13/0265; G06N 3/092
See application file for complete search history.

(56) References Cited

U.S. PATENT DOCUMENTS

2015/0119598 A1    4/2015    Kinsho et al.
2019/0194099 A1    6/2019    Kinsho et al.

OTHER PUBLICATIONS

Baudouy et al. translated (Year: 1988).*
Extended European Search Report corresponding to European Patent Application No. 21169104.3 (5 pages) (dated Sep. 17, 2021).
Baudouy, René, et al., "Synthese diastereoselective d'une composante de la pheromone sexuelle de "l'ecaille rouge de californie" : l'acetate d'isopropenyl-6 methyl-3 decene-9 yle (3S, 6R)", Tetrahedron 44(2), 1988, 471-480.
De Alfonso, Ignacio, et al., "Identification of the Sex Pheromone of the Mealybug *Dysmicoccus grassii leonardi*", J. Agric. Food Chem. 60(48), 2012, 11959-11964.
Dragan, V. A., et al., "Synthesis of the A1 component of the red san jose scale sex pheromone", Bulletin of the Academy of Sciences of the USSR, Division of chemical science 38, 1989, pp. 1038-1041.
Gieselmann, M.J., et al., "Responses of male California red scale to sex pheromone isomers", Journal of Insect Physiology 26(3), 1980, 179-182.
Hinkens, Diane M., et al., "Identification and synthesis of the sex pheromone of the vine mealybug, *Planococcus ficus*", Tetrahedron Letters 42(9), 2001, 1619-1621.
Ho, Hsiao-Yung, et al., "Identification and Synthesis of the Sex Pheromone of the Madeira Mealybug, *Phenacoccus madeirensis green*", Journal of Chemical Ecology 35, 2009, 724-732.
Kefalas, Panagiotis, et al., "Efficient Synthesis of the *Aonidiella aurantii* (Mask.) Sex Pheromone Component: (3S,6RS)-3Methyl6-(1-Methylethenyl)-9-decenyl Acetate", Synthesis 6, 1995, 644-646.
Matsui, Masanao, et al., "New Attempt at the Synthesis of Lavandulol by a Claisen Type Rearrangement", Agro. Biol. Chem. 32(10), 1968, 1246-1249.
Zhang, Aijun, et al., "Sex Pheromone of the Female Pink Hibiscus Mealybug, *Maconellicoccus hirsutus* (Green) (Homoptera: Pseudococcidae): Biological Activity Evaluation", Environmental Entomology 34(2), 2009, 264-270.

* cited by examiner

PROCESS FOR PREPARING 6-ISOPROPENYL-3-METHYL-9-DECENYL ACETATE AND INTERMEDIATES THEREOF

TECHNICAL FIELD

The present invention relates to a process for preparing 6-isopropenyl-3-methyl-9-decenyl acetate, which is a sex pheromone substance of a citrus pest, California red scale (scientific name: *Aonidiella aurantii*).

BACKGROUND ART

Insect sex pheromones are biologically active substances which are usually borne by females to attract males, and exhibit a high attracting activity in a small amount. Sex pheromones are widely utilized as a means for forecasting outbreaks of pests and confirming geographic spread (invasion into a specific area), and also as a means for controlling pests. Widely used methods for controlling pests include a mass trapping method, a lure-and-kill or attract-and-kill method, a lure-and-infect or attract-and-infect method, and a mating disruption method. A naturally occurred sex pheromones can be extracted from an insect individual only in a trace amount. Therefore, it is difficult to use a naturally occurred sex pheromone for a mating disruption method. Before practical use of a sex pheromone, it is required to artificially produce a sufficient amount of a sex pheromone for basic research and also for applications.

California red scale is a pest that has spread widely throughout the world to infest citrus. (3S,6R)-6-Isopropenyl-3-methyl-9-decenyl acetate is reported as a sex pheromone of California red scale (Non-Patent Literature 1 listed below). 6-Isopropenyl-3-methyl-9-decenyl acetate includes four isomers: (3S,6S)-6-isopropenyl-3-methyl-9-decenyl acetate, (3S,6R)-6-isopropenyl-3-methyl-9-decenyl acetate, (3R,6S)-6-isopropenyl-3-methyl-9-decenyl acetate, and (3R,6R)-6-isopropenyl-3-methyl-9-decenyl acetate. It is reported that California red scale is attracted also by a mixture of these four isomers (Non-Patent Literature 1 listed below).

A process for preparing 6-isopropenyl-3-methyl-9-decenyl acetate is reported. For example, in the following Non-Patent Literature 2, the process comprises oxidizing a trisubstituted double bond moiety of citronellol acetate with selenium dioxide and tert-butylhydroperoxide, chlorinating the introduced hydroxyl group with triphenylphosphine and carbon tetrachloride, and subjecting the product to a nucleophilic substitution reaction to form (3S,6RS)-6-isopropenyl-3-methyl-9-decenyl acetate. In the following Non-Patent Literature 3, the process comprises preparing a sulfide compound from citronellol acetate, subjecting the sulfide compound to a 1,2-Stevens rearrangement reaction in the presence of a strong base with meta-chloroperbenzoic acid, oxidating the product with meta-chloroperbenzoic acid to prepare a sulfone compound, and then subjecting the sulfone compound to a trialkylation and a reductive elimination of sulfone to form 6-isopropenyl-3-methyl-9-decenyl acetate.

Further, a process for preparing (3S,6R)-6-isopropenyl-3-methyl-9-decenyl acetate is also reported in the following Non-Patent Literature 4, wherein the process comprises first eight steps including conversion of (−)-dihydrocarvone into a silylenol ether compound, ozone oxidation, reduction with sodium borohydride, and methylation of the carboxylic acid with diazomethane to synthesize (2S, 5R)-5-isopropenyl-2-methyl-8-nonenyl iodide; and then four steps including preparing a nitrile compound using sodium cyanide.

LIST OF THE LITERATURES

Non-Patent Literatures

[Non-Patent Literature 1] M. J. GIESELMANN et al., J. Insect. Physiol. 26, 179 (1980)
[Non-Patent Literature 2] Panagiotis Kefalas et al., Synthesis. 644 (1995)
[Non-Patent Literature 3] V. A. Dragan et al., Russ. Chem. Bull. 38, 1038 (1989)
[Non-Patent Literature 4] R. Boudduy et al., Tetrahedron. 44, 471 (1988)

PROBLEMS TO BE SOLVED BY THE INVENTION

In the process described in Non-Patent Literature 2, selenium dioxide and tert-butylhydroperoxide used in the oxidation reaction of citronellol acetate cause waste which is toxic and environmentally high hazardous and are undesirable for environmental protection. The oxidation reaction may cause explosion and, therefore, is industrially less feasible. Moreover, the oxidation reaction gives a yield as low as 52%.

In the process described in Non-Patent Literature 3, meta-chloroperbenzoic acid used in the oxidation of a sulfide compound may cause explosion. Highly toxic hexamethylphosphoric triamide is used as a solvent for alkylation. These make the process industrially less feasible. The process consists of eight steps and gives a yield as low as 12.3%.

In the process described in Non-Patent Literature 4, synthesis of an intermediate, (2S,5R)-5-isopropenyl-2-methyl-8-nonenyl iodide, requires eight steps which include industrially less unfeasible ozone oxidation is carried out, and use is made of explosive and highly toxic diazomethane. Accordingly, the process is industrially unfavorable. Besides, the formation of (3S,6R)-6-isopropenyl-3-methyl-9-decenyl acetate from (2S,5R)-5-isopropenyl-2-methyl-8-nonenyl iodide requires total four steps. Highly toxic sodium cyanide is used. These make the process industrially less feasible.

Thus, the aforesaid known processes are very difficult to industrially prepare sufficient amount of 6-isopropenyl-3-methyl-9-decenyl acetate.

SUMMARY OF THE INVENTION

The present invention has been made in these circumstances, and aims to provide a process for efficiently and industrially preparing 6-isopropenyl-3-methyl-9-decenyl acetate, without oxidation reaction in a sufficient amount for biological or agricultural activity tests and/or for practical application As a result of the intensive researches to solve the problems, the present inventors have found a 5-isopropenyl-2-methyl-8-nonenyl halide compound; this compound may be prepared efficiently and industrially by a coupling reaction between a nucleophilic agent, 2-isopropenyl-5-hexenyl compound, and a 1,3-dihalo-2-methylpropane compound with no oxidation reaction; and that the 5-isopropenyl-2-methyl-8-nonenyl halide compound is a useful intermediate for the preparation of 6-isopropenyl-3-methyl-9-decenyl acetate. Thus, the present invention has been invented.

One aspect of the present invention provides a process for preparing 6-isopropenyl-3-methyl-9-decenyl acetate of the following formula (3):

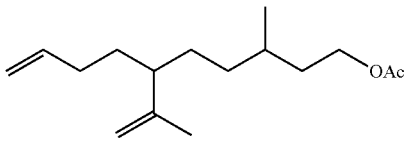
(3)

wherein Ac represents an acetyl group,
the process comprising steps of:
preparing a nucleophilic reagent, 5-isopropenyl-2-methyl-8-nonenyl compound, of the following general formula (1):

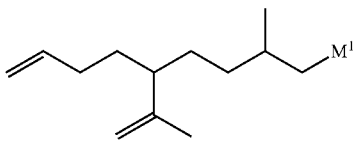
(1)

wherein $M^1$ represents Li, $MgZ^1$, $ZnZ^1$, Cu, $CuZ^1$, or $CuLiZ^1$, wherein $Z^1$ represents a halogen atom or a 5-isopropenyl-2-methyl-8-nonenyl group,
from a 5-isopropenyl-2-methyl-8-nonenyl halide compound of the following general formula (4):

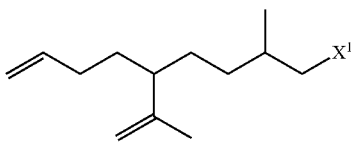
(4)

wherein $X^1$ represents a halogen atom;
subjecting the nucleophilic reagent (1), 5-isopropenyl-2-methyl-8-nonenyl compound, to an addition reaction with at least one electrophilic reagent selected from the group consisting of formaldehyde, paraformaldehyde, and 1,3,5-trioxane, followed by a hydrolysis reaction to form 6-isopropenyl-3-methyl-9-decenol of the following formula (2):

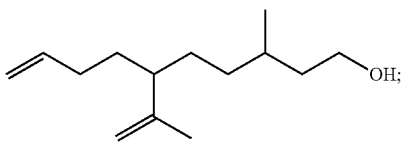
(2)

and
acetylating 6-isopropenyl-3-methyl-9-decenol (2) to form 6-isopropenyl-3-methyl-9-decenyl acetate (3).

Another aspect of the present invention provides a process for preparing a 5-isopropenyl-2-methyl-8-nonenyl halide compound of the following general formula (4):

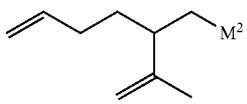
(4)

wherein $X^1$ represents a halogen atom,
the process comprising steps of:
subjecting a nucleophilic reagent, 2-isopropenyl-5-hexenyl compound, of the following general formula (5):

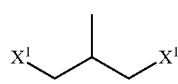
(5)

wherein $M^2$ represents Li, $MgZ^2$, $ZnZ^2$, Cu, $CuZ^2$, or $CuLiZ^2$, wherein $Z^2$ represents a halogen atom or a 2-isopropenyl-5-hexenyl group,
to a coupling reaction with a 1,3-dihalo-2-methylpropane compound of the following general formula (6):

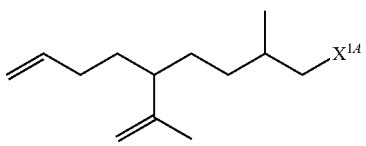
(6)

wherein $X^1$ represents, independently of each other, a halogen atom,
to form 5-isopropenyl-2-methyl-8-nonenyl halide compound (4).

Another aspect of the present invention provides a 5-isopropenyl-2-methyl-8-nonenyl halide compound of the following general formula (4'):

(4')

wherein $X^{1A}$ represents a chlorine atom or a bromine atom.
In addition, another aspect of the present invention provides a process for preparing 6-isopropenyl-3-methyl-9-decenyl acetate (3), the process comprising steps of:
subjecting the nucleophilic reagent (1), 5-isopropenyl-2-methyl-8-nonenyl compound, to an addition reaction with at least one electrophilic reagent selected from the group consisting of formaldehyde, paraformaldehyde, and 1,3,5-trioxane, followed by a hydrolysis reaction to form 6-isopropenyl-3-methyl-9-decenol (2); and
acetylating 6-isopropenyl-3-methyl-9-decenol (2) to form 6-isopropenyl-3-methyl-9-decenyl acetate (3).

The present invention provides a process for efficiently and industrially preparing 6-isopropenyl-3-methyl-9-decenyl acetate, without an oxidation reaction that is industrially unfavorable in view of safety, economy, and environmental burden. The present invention also provides a 5-isopropenyl-2-methyl-8-nonenyl halide compound, which is a useful intermediate in the preparation of 6-isopropenyl-3-methyl-9-decenyl acetate, and a process for preparing the same.

DETAILED DESCRIPTION OF THE PREFERRED EMBODIMENTS

Embodiments of the present invention will be explained hereinafter in detail. It should be understood that the present invention is not limited to or by the embodiments. In the intermediates, the reagents, and the target compounds represented by the chemical formulae in the present specification, there may be some stereoisomers such as enantiomers or diastereoisomers. Unless otherwise stated, each chemical formula shall be interpreted to represent all of these isomers. The isomer may be either alone or in combination thereof.

I. First, a process for preparing a 5-isopropenyl-2-methyl-8-nonenyl halide compound of the following general formula (4), which is a starting material in a process for preparing 6-isopropenyl-3methyl-9-decenyl acetate, will be explained hereinafter.

The 5-isopropenyl-2-methyl-8-nonenyl halide compound (4) is obtained by subjecting a nucleophilic reagent, 2-isopropenyl-5-hexenyl compound, of the following general formula (5) to a coupling reaction with a 1,3-dihalo-2-methylpropane compound of the following general formula (6).

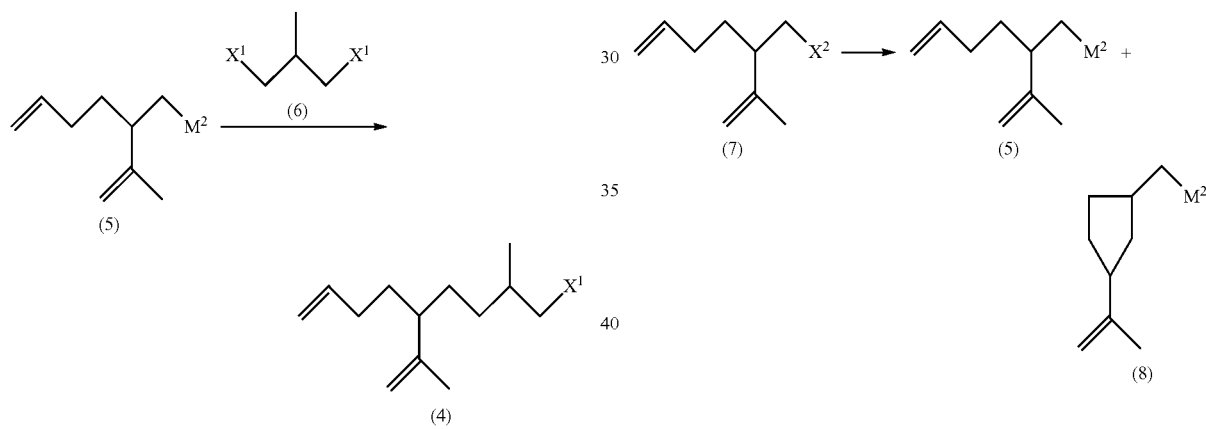

First, the nucleophilic reagent (5), 2-isopropenyl-5-hexenyl compound, will be explained hereinafter.

$M^2$ represents Li, $MgZ^2$, $ZnZ^2$, Cu, $CuZ^2$ or $CuLiZ^2$, and $Z^2$ represents a halogen atom or a 2-isopropenyl-5-hexenyl group. Examples of the halogen atom include a chlorine atom, a bromine atom, and an iodine atom.

The nucleophilic reagent (5), 2-isopropenyl-5-hexenyl compound, is preferably an organolithium reagent such as 2-isopropenyl-5-hexenyllithium; and an organomagnesium reagent, i.e., a Grignard reagent, such as a 2-isopropenyl-5-hexenylmagnesium halide compound, in terms of the reactivity, selectivity, and/or easiness of preparation, more preferably a Grignard reagent in terms of the economy and/or easiness of preparation.

Specific examples of the 2-isopropenyl-5-hexenylmagnesium halide compound include 2-isopropenyl-5-hexenylmagnesium chloride, 2-isopropenyl-5-hexenylmagnesium bromide, and 2-isopropenyl-5-hexenylmagnesium iodide.

The nucleophilic reagent (5), 2-isopropenyl-5-hexenyl compound, may be prepared, for example, from a 2-isopropenyl-5-hexenyl halide compound of the following general formula (7).

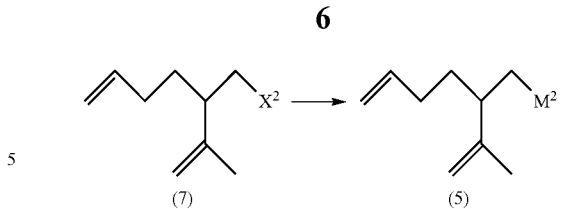

$X^2$ in formula (7) represents a halogen atom. Examples of the halogen atom include a chlorine atom, a bromine atom, and an iodine atom. In view of the reactivity, a chlorine atom and a bromine atom are preferred.

Specific examples of the 2-isopropenyl-5-hexenyl halide compound (7) include 2-isopropenyl-5-hexenyl chloride, 2-isopropenyl-5-hexenyl bromide, and 2-isopropenyl-5-hexenyl iodide. In view of easiness of preparation and/or stability, 2-isopropenyl-5-hexenyl chloride and 2-isopropenyl-5-hexenyl bromide are preferred.

The 2-isopropenyl-5-hexenyl halide compound (7) may be prepared, for example, by subjecting 2-isopropenyl-5-hexenol to a substitution reaction with a halogenating agent (see Synthetic Example 1 below).

In the step of preparing the nucleophilic reagent (5), 2-isopropenyl-5-hexenyl compound, from the 2-isopropenyl-5-hexenyl halide compound (7), a cyclic nucleophilic compound of the following general formula (8) might be by-produced.

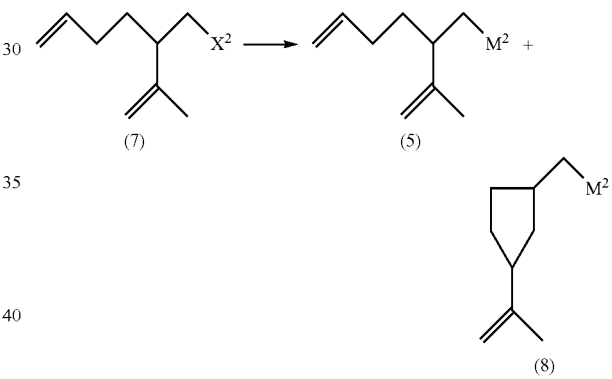

In the coupling reaction between the nucleophilic reagent (5), 2-isopropenyl-5-hexenyl compound, and the 1,3-dihalo-2-methylpropane compound (6), a mixture of the nucleophilic reagent (5), 2-isopropenyl-5-hexenyl compound, and the by-produced cyclic nucleophilic reagent (8) may be used.

When the mixture is used, the by-produced cyclic nucleophilic reagent (8) may cause a coupling reaction with the 1,3-dihalo-2-methylpropane compound (6) to further by-produce a cyclic halide compound of the following general formula (9).

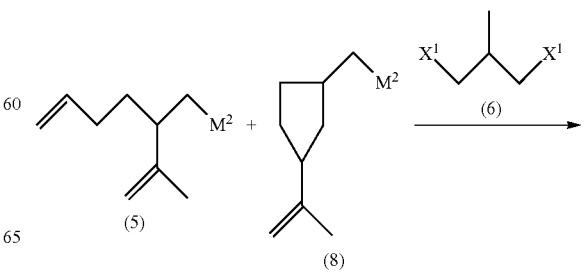

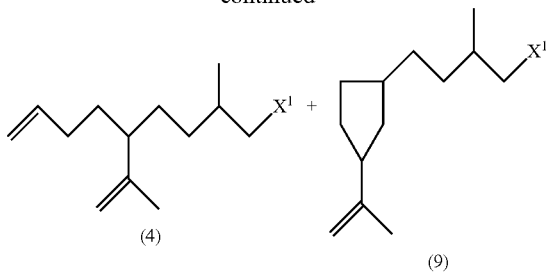

If the cyclic nucleophilic reagent (8) is much by-produced, a yield of the target compound, 5-isopropenyl-2-methyl-8-nonenyl halide compound (4), will be low. Therefore, in the step of preparing the nucleophilic reagent (5), 2-isopropenyl-5-hexenyl compound, optimal conditions might be adopted to reduce an amount of the by-produced cyclic nucleophilic reagent (8). Examples of the optimal conditions include a reaction temperature of 90° C. or below and/or 100 g or more of a solvent used in the preparation of the nucleophilic reagent (5), 2-isopropenyl-5-hexenyl compound, per mol of the nucleophilic reagent (5), 2-isopropenyl-5-hexenyl compound.

The cyclic halide compound (9) by-produced from the cyclic nucleophilic reagent (8) in the coupling reaction may also be removed by purification such as distillation.

In the coupling reaction between the nucleophilic reagent (5), 2-isopropenyl-5-hexenyl compound, and the 1,3-dihalo-2-methylpropane compound (6), an organometallic reagent comprising a metal element of the Group I or II or a transition metal element is typically used.

When a transition metal compound used in the coupling reaction is used with the nucleophilic reagent (5), 2-isopropenyl-5-hexenyl compound, may be prepared by subjecting an organolithium reagent or an organomagnesium reagent to a metal exchange reaction with a stoichiometric amount (1 mol) of a transition metal compound or may be formed in situ by reacting an organolithium reagent or a Grignard reagent with a very small amount, such as 0.0001 or more, of a transition metal compound.

Examples of the transition metal compound include those comprising copper, iron, nickel, palladium, zinc, or silver. Preferred are cuprous halides such as copper(I) chloride, copper(I) bromide, and copper(I) iodide; cupric halides such as copper(II) chloride, copper(II) bromide, and copper(II) iodide; copper cyanides such as copper(I) cyanide and copper(II) cyanide; copper oxides such as copper(I) oxide and copper(II) oxide; and copper compounds such as dilithium tetrachlorocuprate ($Li_2CuCl_4$). In view of the reactivity, cuprous halides and cupric halides are more preferred.

An amount of the transition metal compound may be from a very small amount, such as from 0.0001 to 1-time a stoichiometric amount relative to the amount of the 2-isopropenyl-5-hexenyl compound comprising a metal element of Group I or II, or even a 100-times excessive amount. A small amount below a stoichiometric amount is preferred.

When the transition metal compound is used in the coupling reaction, a phosphorus compound may also be used in view of enhancement solubility of the transition metal compound in a solvent.

Examples of the phosphorus compounds include trialkyl phosphites such as triethyl phosphite; and triarylphosphine such as triphenylphosphine.

The phosphorus compound may be used alone or in combination thereof, if necessary. The phosphorus compound may be commercially available one.

An amount of the phosphorus compound used is from 0.001 to 1000 mol parts per 100 parts of the transition metal compound in view of the reactivity.

In the coupling reaction, 0.001 to 1,000 mol of a lithium salt such as lithium chloride, lithium bromide, or lithium iodide per mol of the 1,3-dihalo-2-methylpropane compound (6) may be used as a catalyst for the reaction.

An amount of the nucleophilic reagent (5), 2-isopropenyl-5-hexenyl compound, may be arbitrarily set in view of the reagent, reaction conditions, a reaction yield, economy such as prices of intermediates, and/or easiness of purification of the target compound from a reaction mixture, and is preferably from 0.2 to 100 mol, more preferably from 0.5 to 20 mol, and even more preferably from 0.8 to 2 mol, per mol of the 1,3-dihalo-2-methylpropane compound (6).

Next, the 1,3-dihalo-2-methylpropane compound (6) will be explained hereinafter.

$X^1$ represents, independently of each other, a halogen atom. Examples of the halogen atom preferably include a chlorine atom, a bromine atom, and an iodine atom.

A combination of two $X^1$ is preferably a combination of a bromine atom and a chlorine atom, a combination of a bromine atom and a bromine atom, a combination of an iodine atom and a chlorine atom, or a combination of an iodine atom and a bromine atom, in view of the reactivity and/or selectivity.

Specific examples of the 1,3-dihalo-2-methylpropane compound (6) include 1,3-dichloro-2-methylpropane, 1-bromo-3-chloro-2-methylpropane, 1,3-dibromo-2-methylpropane, 1-iodo-3-chloro-2-methylpropane, 1-iodo-3-bromo-2-methylpropane, and 1,3-diiodo-2-methylpropane. In view of the reactivity, 1-bromo-3-chloro-2-methylpropane, 1,3-dibromo-2-methylpropane, 1-iodo-3-chloro-2-methylpropane, and 1-iodo-3-bromo-2-methylpropane are preferred.

The 1,3-dihalo-2-methylpropane compound (6) may be commercially available one or may be prepared in a known synthetic method, for example, a substitution reaction of 2-methyl-1,3-diol with a halogenating agent.

Next, the coupling reaction will be explained hereinafter.

The coupling reaction is typically carried out in the presence of a solvent and, if necessary, under heating or cooling.

The solvent used in the coupling reaction is preferably an ether such as diethyl ether, di-n-butyl ether, t-butyl methyl ether, cyclopentyl methyl ether, tetrahydrofuran, or 1,4-dioxane; or a mixed solvent of such a solvent with a hydrocarbon such as hexane, heptane, benzene, toluene, xylene, or cumene, and an aprotic polar solvent such as N,N-dimethylformamide (DMF), N,N-dimethylacetamide, N,N-dimethylpropionamide, 1,3-dimethyl-2-imidazolidinone (DMI), dimethyl sulfoxide (DMSO), and hexamethylphosphoric triamide (HMPA).

An amount of the solvent used is not particularly limited and is preferably from 10 to 1,000,000 g, more preferably from 100 to 100,000 g, and even more preferably from 150 to 10,000 g, per mol of the nucleophilic reagent (5), 2-isopropenyl-5-hexenyl compound.

A reaction temperature of the coupling reaction is preferably from −78° C. to a boiling point of the solvent, more preferably from −10 to 100° C.

A reaction time of the coupling reaction may be arbitrarily set and may be optimized by monitoring the reaction progress with gas chromatography (GC) or thin layer chromatography (TLC). The reaction time is typically and preferably from 5 minutes to 240 hours.

Next, the 5-isopropenyl-2-methyl-8-nonenyl halide compound (4) will be explained hereinafter.

$X^1$ represents a halogen atom. Examples of the halogen atom include a chlorine atom, a bromine atom, and an iodine atom.

Specific examples of the 5-isopropenyl-2-methyl-8-nonenyl halide compound (4) include 5-isopropenyl-2-methyl-8-nonenyl chloride, 5-isopropenyl-2-methyl-8-nonenyl bromide, 5-isopropenyl-2-methyl-8-nonenyl iodide, and a 5-isopropenyl-2-methyl-8-nonenyl halide compound of the following general formula (4'):

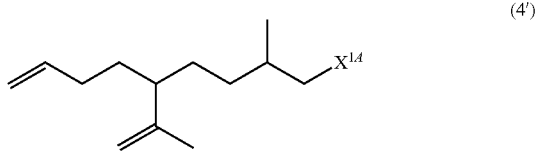

wherein $X^{1A}$ represents a chlorine atom or a bromine atom. In view of the reactivity, the 5-isopropenyl-2-methyl-8-nonenyl halide compound (4') is preferred.

When the 5-isopropenyl-2-methyl-8-nonenyl halide compound (4) obtained in the coupling reaction has a sufficient purity, the 5-isopropenyl-2-methyl-8-nonenyl halide compound (4) may be used as such in a subsequent step. Alternatively, the crude product may be purified in any purification method used in usual organic synthesis, such as distillation or various chromatography. Distillation is particularly preferred in view of the industrial economy.

II. Step of preparing the nucleophilic reagent, 5-isopropenyl-2-methyl-8-nonenyl compound, of the following general formula (1) from the 5-isopropenyl-2-methyl-8-nonenyl halide compound (4) will be explained hereinafter.

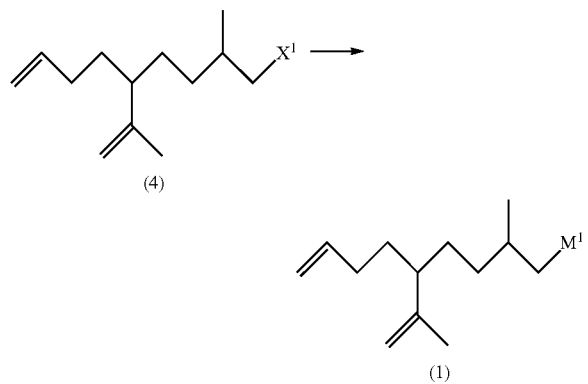

First, the nucleophilic reagent (1), 5-isopropenyl-2-methyl-8-nonenyl compound, will be explained hereinafter.

$M^1$ represents Li, $MgZ^1$, $ZnZ^1$, Cu, $CuZ^1$, or $CuLiZ^1$, wherein $Z^1$ represents a halogen atom or a 5-isopropenyl-2-methyl-8-nonenyl group. Examples of the halogen atom include a chlorine atom, a bromine atom, and an iodine atom.

The nucleophilic reagent (1), 5-isopropenyl-2-methyl-8-nonenyl compound, is preferably an organolithium reagent such as 5-isopropenyl-2-methyl-8-nonenyllithium; or an organomagnesium reagent, i.e., a Grignard reagent, such as a 5-isopropenyl-2-methyl-8-nonenylmagnesium halide, in view of the reactivity, selectivity, and/or easiness of preparation. The 5-isopropenyl-2-methyl-8-nonenylmagnesium halide is more preferred.

Specific examples of the 5-isopropenyl-2-methyl-8-nonenylmagnesium halide compound include 5-isopropenyl-2-methyl-8-nonenylmagnesium chloride, 5-isopropenyl-2-methyl-8-nonenylmagnesium bromide, and 5-isopropenyl-2-methyl-8-nonenylmagnesium iodide.

The nucleophilic reagent (1), 5-isopropenyl-2-methyl-8-nonenyl compound, may be prepared in a conventional method from its corresponding halide, 5-isopropenyl-2-methyl-8-nonenyl halide compound (4).

III. Next, explained is a step of subjecting the nucleophilic reagent (1), 5-isopropenyl-2-methyl-8-nonenyl compound, to an addition reaction with at least one electrophilic reagent selected from the group consisting of formaldehyde, paraformaldehyde, and 1,3,5-trioxane, followed by a hydrolysis reaction to form 6-isopropenyl-3-methyl-9-decenol of the following formula (2).

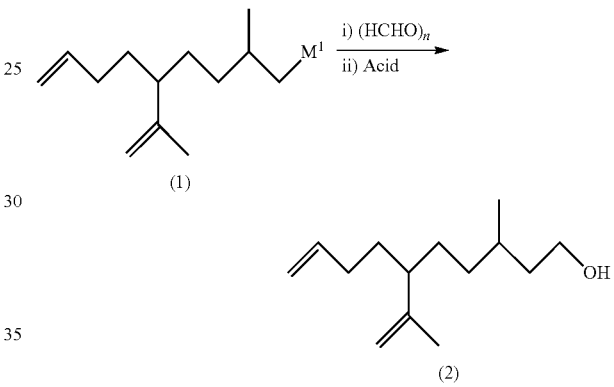

In the addition reaction, the transition metal compound may be added, if necessary.

Examples of the electrophilic reagent used in the addition reaction include formaldehyde equivalents such as formaldehyde, paraformaldehyde, and 1,3,5-trioxane.

Formaldehyde may be in a gaseous form obtained by heating a formaldehyde equivalent selected from paraformaldehyde and 1,3,5-trioxane or in a liquid form obtained by dissolving the gas in a solvent used in the addition reaction. Alternatively, at least one formaldehyde equivalent selected from paraformaldehyde and 1,3,5-trioxane may be used as such in the addition reaction. A mixture of two or more formaldehyde equivalents selected from formaldehyde, paraformaldehyde, and 1,3,5-trioxane may be used.

An amount of the electrophilic reagent used may be arbitrarily set, depending upon the reagents, reaction conditions, a reaction yield, economy such as prices of intermediates, easiness of purification of the target compound from a reaction mixture, and/or formation of by-products and is preferably from 0.8 to 100 mol, more preferably from 0.9 to 10 mol, and even more preferably from 1.0 to 2.0 mol, per mol of the nucleophilic reagent (1), 5-isopropenyl-2-methyl-8-nonenyl compound.

The addition reaction is typically carried out in the presence of a solvent and, if necessary, under heating or cooling.

The solvent used in the addition reaction is preferably an ether such as diethyl ether, di-n-butyl ether, t-butyl methyl ether, cyclopentyl methyl ether, tetrahydrofuran, or 1,4- dioxane, or a mixed solvent of such a solvent with a hydrocarbon such as hexane, heptane, benzene, toluene, xylene, and cumene; and an aprotic polar solvent such as N,N-dimethylformamide (DMF), N,N-dimethylacetamide, N,N-dimethylpropionamide, 1,3-dimethyl-2-imidazolidinone (DMI), dimethyl sulfoxide (DMSO), and hexamethylphosphoric triamide (HMPA).

An amount of the solvent used is not particularly limited and is preferably from 10 to 1,000,000 g, more preferably from 100 to 100,000 g, and even more preferably from 150 to 10,000 g, per mol of the nucleophilic reagent (1), 5-isopropenyl-2-methyl-8-nonenyl compound.

A reaction temperature of the addition reaction is preferably from −78° C. to a boiling point of the solvent, more preferably from −10 to 150° C. When a formaldehyde equivalent selected from paraformaldehyde and 1,3,5-trioxane is used in the addition reaction, the reaction temperature is preferably from 30 to 150° C., because the reaction is carried out while producing formaldehyde in situ.

A reaction time of the addition reaction may be arbitrarily set and may be optimized by monitoring the reaction progress with gas chromatography (GC) or thin layer chromatography (TLC). The reaction time is typically and preferably from 5 minutes to 240 hours.

The hydrolysis reaction is carried out typically by subjecting the reaction mixture obtained from the addition reaction to an acidic condition.

Examples of the acid used in the hydrolysis reaction include inorganic acids such as ammonium chloride, hydrochloric acid, hydrobromic acid, hydroiodic acid, sulfuric acid, nitric acid, boric acid, and phosphoric acid; and organic acids such as formic acid, acetic acid, propionic acid, oxalic acid, trifluoroacetic acid, methanesulfonic acid, benzenesulfonic acid, p-toluenesulfonic acid, and naphthalenesulfonic acid.

The acid may be used alone or in combination thereof, if necessary. The acid may be commercially available one.

An amount of the acid used in the hydrolysis reaction is not particularly limited as long as the amount is sufficient to hydrolyze the compound, and is preferably from 1.0 to 100 mol per mol of the nucleophilic reagent (1), 5-isopropenyl-2-methyl-8-nonenyl compound, in view of the sufficient progress of the hydrolysis reaction.

When 6-isopropenyl-3-methyl-9-decenol (2) obtained from the addition reaction and the hydrolysis reaction has a sufficient purity, such may be used as such as a crude product in a subsequent step, or the crude product may be purified in any purification method used in ordinary organic synthesis, such as distillation and/or various chromatography. When the purification is carried out, distillation is particularly preferred in view of the industrial economy.

IV. Next, is explained a step of acetylating 6-isopropenyl-3-methyl-9-decenol (2) to form 6-isopropenyl-3-methyl-9-decenyl acetate of the following formula (3).

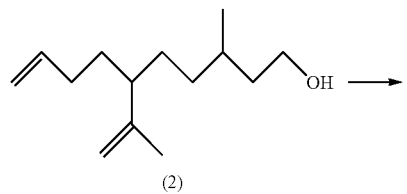

(2)

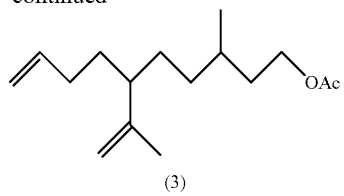

(3)

The acetylation may be done in any known manner for preparing an acetate, for example, (A) a reaction with an acetylating agent, (B) a dehydration reaction with acetic acid, (C) a transesterification with an acetate ester, and (D) a conversion of 6-isopropenyl-3-methyl-9-decenol (2) into an alkylating agent, followed by an acetoxylation with acetic acid or a metal acetate salt. The aforesaid manners, (A) to (D), will be explained hereinafter in detail.

(A) Reaction with an Acetylating Agent

The reaction with an acetylating agent may be carried out in a method of reacting 6-isopropenyl-3-methyl-9-decenol (2) with an acetylating agent in the presence of a base in a single solvent or a mixed solvent, or a method of reacting 6-isopropenyl-3-methyl-9-decenol (2) with an acetylating agent in the presence of a catalyst in a single solvent or a mixed solvent.

Examples of the acetylating agent include acetic chloride, acetic bromide, and acetic anhydride.

An amount of the acetylating agent used is preferably from 1.0 mol to 30.0 mol, more preferably from 1.0 mol to 5.0 mol, per mol of 6-isopropenyl-3-methyl-9-decenol (2) in view of the economy.

Examples of the base used in the reaction with an acetylating agent include amines such as triethylamine, pyridine, N,N-dimethylaminopyridine, and N,N-dimethylaniline; organolithium compounds such as n-butyllithium, methyllithium, and phenyllithium; metal hydroxides such as sodium hydroxide and potassium hydroxide; and metal carbonates such as potassium carbonate, sodium carbonate, and sodium bicarbonate.

An amount of the base used is preferably from 1.0 mol to 50.0 mol, more preferably from 1.0 mol to 10.0 mol, per mol of 6-isopropenyl-3-methyl-9-decenol (2) in view of the economy.

A catalyst may be used when the acetylating agent is acetic anhydride. Examples of the catalyst include inorganic acids such as hydrochloric acid, hydrobromic acid, nitric acid, and sulfuric acid; sulfonic acids such as methanesulfonic acid, benzenesulfonic acid, and p-toluenesulfonic acid; Lewis acids such as aluminum trichloride, aluminum isopropoxide, zinc chloride, boron trifluoride, boron trichloride, tin tetrachloride, dibutyltin dichloride, titanium tetrachloride, and titanium(IV) isopropoxide; and metal acetate salts such as sodium acetate and potassium acetate.

An amount of the catalyst used in the reaction with an acetylating agent is preferably from 0.001 mol to 1.0 mol, more preferably from 0.005 mol to 0.2 mol, per mol of 6-isopropenyl-3-methyl-9-decenol (2) in view of the economy.

Examples of the solvent used in the reaction with the acetylating agent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutylketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The solvent may be commercially available one. Depending on the acetylating agent to be used, the reaction may be carried out without a solvent.

An amount of the solvent used in the reaction with the acetylating agent is preferably from 0.0 g to 2000.0 g, more preferably from 0.0 g to 500.0 g, per mol of 6-isopropenyl methyl-9-decenol (2) in view of the economy.

A reaction temperature of the reaction with the acetylating agent is preferably from −78° C. to a boiling point of the solvent, more preferably from −30° C. to 80° C., in view of the reactivity and yield.

A reaction time of the reaction with the acetylating agent may be arbitrarily set and may be optimized by monitoring the reaction progress with gas chromatography (GC) or thin layer chromatography (TLC). The reaction time is typically and preferably from 5 minutes to 240 hours.

(B) Dehydration Reaction with Acetic Acid

The dehydration reaction with acetic acid may be typically carried out in the presence of a catalyst such as another acid and a Lewis acid.

Examples of the catalyst include inorganic acids such as hydrochloric acid, hydrobromic acid, nitric acid, and sulfuric acid; organic acids such as trichloroacetic acid, trifluoroacetic acid, methanesulfonic acid, benzenesulfonic acid, and p-toluenesulfonic acid; and Lewis acids such as aluminum trichloride, dichloroaluminum ethoxide, aluminum ethoxide, aluminum isopropoxide, zinc diisopropoxide, zinc diethoxide, zinc dimethoxide, zinc chloride, boron trifluoride, boron trichloride, tin tetrachloride, dibutyltin dichloride, dibutyltin dimethoxide, dibutyltin oxide, titanium tetrachloride, titanium tetrabromide, titanium(IV) methoxide, titanium(IV) ethoxide, and titanium(IV) isopropoxide.

The catalyst may be used alone or in combination thereof, if necessary. The catalyst may be commercially available one.

An amount of the catalyst used is preferably from 0.001 mol to 1.0 mol, more preferably from 0.05 mol to 0.1 mol, per mol of 6-isopropenyl-3-methyl-9-decenol (2) in view of the economy and reactivity.

The dehydration reaction with acetic acid may be carried out, while removing water by-produced in the reaction, for example, by azeotropically distilling off the solvent used and water at normal pressure or at a reduced pressure, or by adding a dehydrating agent such as anhydrous magnesium sulfate, a molecular sieve, or dicyclohexylcarbodiimide into the reaction system.

Examples of the solvent used in the dehydration reaction include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; and ester solvents such as ethyl acetate and butyl acetate.

The solvent may be used alone or in combination thereof, if necessary. The solvent may be commercially available one. The dehydration reaction may be carried out without a solvent.

An amount of the solvent used is preferably from 0.0 g to 2000.0 g, more preferably from 0.0 g to 500.0 g, per mol of 6-isopropenyl-3-methyl-9-decenol (2) in view of the economy.

A reaction temperature of the dehydration reaction may be appropriately selected, depending on a catalyst to be used. Typically, the reaction temperature is preferably from −30° C. to 200° C., more preferably from 25° C. to 100° C., in view of the reactivity and yield. When water by-produced in the reaction is removed by azeotropically distilling off water and the solvent, the reaction temperature is preferably an azeotropic boiling point or above at normal pressure or at a reduced pressure.

A reaction time of the dehydration reaction may be arbitrarily set and may be optimized by monitoring the reaction progress with gas chromatography (GC) or thin layer chromatography (TLC). The reaction time is typically and preferably from 5 minutes to 240 hours.

(C) Transesterification with an Acetate Ester

The transesterification with an acetate ester is typically carried out in the presence of a catalyst and can be facilitated by removing an alcohol formed from the acetate ester at normal pressure or at a reduced pressure.

Examples of the acetate ester include methyl acetate, ethyl acetate, propyl acetate, butyl acetate, and phenyl acetate. Among these acetate esters, methyl acetate and ethyl acetate are preferred in view of the economy, the reactivity, and easiness of removal of an alcohol formed from the acetate ester.

An amount of the acetic ester used is preferably from 1.0 mol to 30.0 mol, more preferably from 1.0 mol to 5.0 mol, per mol of 6-isopropenyl-3-methyl-9-decenol (2).

Examples of the catalyst used in the transesterification include acids such as hydrochloric acid, sulfuric acid, trifluoroacetic acid, methanesulfonic acid, benzenesulfonic acid, p-toluenesulfonic acid, and Amberlyst 15; alkali metal salts of alcohols such as sodium methoxide, sodium ethoxide, and potassium t-butoxide; metal carboxylate salts such as sodium acetate, potassium acetate, calcium acetate, tin acetate, zinc acetate, and aluminum acetate; and Lewis acids such as aluminum trichloride, aluminum ethoxide, aluminum isopropoxide, zinc diisopropoxide, zinc diethoxide, zinc dimethoxide, zinc chloride, boron trifluoride, boron trichloride, tin tetrachloride, dibutyltin dichloride, dibutyltin dimethoxide, dibutyltin oxide, titanium tetrachloride, titanium tetrabromide, titanium(IV) methoxide, titanium(IV) ethoxide, and titanium(IV) isopropoxide.

An amount of the catalyst used is preferably from 0.001 mol to 1.0 mol, more preferably from 0.005 mol to 0.05 mol, per mol of 6-isopropenyl-3-methyl-9-decenol (2).

Examples of a solvent used in the transesterification include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; and ester solvents such as ethyl acetate and butyl acetate.

The solvent may be used alone or in combination thereof, if necessary. The solvent may be commercially available one. The transesterification may be carried out only with alcohol compound, the acetate ester, and the catalyst, without any solvent.

An amount of the solvent used is preferably from 0.0 g to 2000.0 g, more preferably from 0.0 g to 500.0 g, per mol of 6-isopropenyl-3-methyl-9-decenol (2) in view of the economy.

A reaction temperature of the transesterification may be appropriately selected, depending on the acetate ester and the catalyst to be used. Typically, the reaction temperature is preferably from 0° C. to 200° C., more preferably from 50°

C. to 160° C. When the transesterification is facilitated by removing the alcohol compound by-produced from the acetate ester, the reaction temperature is preferably a boiling point or above of the alcohol to be removed at normal pressure or at a reduced pressure.

A reaction time of the transesterification may be arbitrarily set and may be optimized by monitoring the reaction progress with gas chromatography (GC) or thin layer chromatography (TLC). The reaction time is typically and preferably from 5 minutes to 240 hours.

(D) Conversion of 6-isopropenyl-3-methyl-9-decenol (2) into an Alkylating Agent, Followed by Acetoxylation with Acetic Acid or a Metal AScetate Salt Typically, 6-isopropenyl-3-methyl-9-decenol (2) is converted into its corresponding alkylating agent such as, for example, a halide such as a chloride, a bromide, and an iodide, and a sulfonate ester such as a methanesulfonate ester, a benzenesulfonate ester, or a p-toluenesulfonate ester, and the obtained alkylating agent is reacted with acetic acid in the presence of a base. The acetoxylation reaction may be also carried out without a base, but using an available metal acetate salt such as sodium acetate or potassium acetate instead of acetic acid.

The conversion of 6-isopropenyl-3-methyl-9-decenol (2) into a corresponding alkylating agent and the acetoxylation with acetic acid or a metal acetate salt may be carried out in consecutive procedures of the conversion and the acetoxylation. Alternatively, after the conversion of 6-isopropenyl-3-methyl-9-decenol (2) into a corresponding alkylating agent, the organic phase is washed, the solvent is removed and the alkylating agent is, if necessary, purified, and then acetoxylated with acetic acid.

The conversion of 6-isopropenyl-3-methyl-9-decenol (2) into its corresponding alkylating agent may be a conversion of 6-isopropenyl-3-methyl-9-decenol (2) with a halogenating agent into its chloride, a bromide, or an iodide, or a conversion of 6-isopropenyl-3-methyl-9-decenol (2) with a sulfonylating agent into a sulfonate ester.

Examples of the halogenating agent include chlorinating agents such as hydrochloric acid, phosphorous trichloride, thionyl chloride, carbon tetrachloride, methanesulfonyl chloride, and p-toluenesulfonyl chloride; brominating agents such as hydrobromic acid, phosphorus tribromide, thionyl bromide, and carbon tetrabromide; and iodinating agents such as hydroiodic acid, potassium iodide, and phosphorus triiodide.

Examples of the sulfonylating agent include methanesulfonyl chloride, benzenesulfonyl chloride, and p-toluenesulfonyl chloride.

An amount of the halogenating agent or the sulfonylating agent used is preferably from 1.0 mol to 50.0 mol, more preferably from 1.0 mol to 10.0 mol, per mol of 6-isopropenyl-3-methyl-9-decenol (2) in view of the economy.

An amount of the acetic acid or metal acetate salt used in the acetoxylation reaction of the obtained alkylating agent is preferably from 1.0 mol to 50.0 mol, more preferably from 1.0 mol to 10.0 mol, per mol of the alkylating agent in view of the economy.

Examples of the base used in the acetoxylation reaction of the obtained alkylating agent include amines such as triethylamine, pyridine, N,N-dimethylaminopyridine, and dimethylaniline; organolithium compounds such as n-butyllithium, methyllithium, and phenyllithium; metal hydroxides such as sodium hydroxide and potassium hydroxide; metal carbonates such as potassium carbonate, sodium carbonate, and sodium bicarbonate; and metal hydrides such as sodium hydride and potassium hydride.

An amount of the base used in the acetoxylation reaction of the obtained alkylating agent is preferably from 1.0 mol to 50.0 mol, more preferably from 1.0 mol to 10.0 mol, per mol of the alkylating agent in view of the economy.

Examples of the solvent used in the conversion into the alkylating agent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The solvent may be commercially available one. The conversion may be carried out without a solvent.

An amount of the solvent used is preferably from 0.0 g to 2000.0 g, more preferably from 0.0 g to 500.0 g, per mol of 6-isopropenyl-3-methyl-9-decenol (2) in view of the economy.

A reaction temperature of the conversion into the alkylating agent is preferably from −30° C. to 250°, more preferably from 0° C. to 180° C., in view of the reactivity and yield.

A reaction time of the conversion into the alkylating agent may be arbitrarily set and may be optimized by monitoring the reaction progress with gas chromatography (GC) or thin layer chromatography (TLC). The reaction time is typically and preferably from 5 minutes to 240 hours.

Examples of a solvent used in the acetoxylation reaction of the obtained alkylating agent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The solvent may be commercially available one. The acetoxylation reaction may be carried out without a solvent.

An amount of the solvent used in the acetoxylation reaction of the obtained alkylating agent is preferably from 0.0 g to 2000.0 g, more preferably from 0.0 g to 500.0 g, per mol of the alkylating agent in view of the economy.

A reaction temperature of the acetoxylation reaction of the obtained alkylating agent is preferably from −30° C. to 250° C., more preferably from 25° C. to 180° C., in view of the reactivity and yield.

A reaction time of the acetoxylation reaction of the obtained alkylating agent may be arbitrarily set and may be optimized by monitoring the reaction progress with gas chromatography (GC) or thin layer chromatography (TLC). The reaction time is typically and preferably from 5 minutes to 240 hours.

A reaction time of the acetylation may be arbitrarily set and may be optimized by monitoring the reaction progress with gas chromatography (GC) or thin layer chromatography (TLC). The reaction time is typically preferably from 5 minutes to 240 hours.

A crude product, 6-isopropenyl-3-methyl-9-decenyl acetate (3) obtained in the acetylation, may be purified in any purification method used in ordinary organic synthesis, such as distillation and/or various chromatography. When the purification is carried out, distillation is particularly preferred in view of the industrial economy.

Thus, there are provided a process for efficiently and industrially preparing 6-isopropenyl-3-methyl-9-decenyl acetate (3), and 5-isopropenyl-2-methyl-8-nonenyl halide compound (4), which is a useful intermediate material for the process.

6-Isopropenyl-3-methyl-9-decenyl acetate (3) has four isomers: (3S,6S)-6-isopropenyl-3-methyl-9-decenyl acetate, (3S,6R)-6-isopropenyl-3-methyl-9-decenyl acetate, (3R,6S)-6-isopropenyl-3-methyl-9-decenyl acetate, and (3R,6R)-6-isopropenyl-3-methyl-9-decenyl acetate. The isomer may be used alone or in combination thereof.

EXAMPLES

The present invention will be further described with reference to the following Examples. It should be understood that the present invention is not limited to or by the Examples.

The term "purity" as used herein means an area percentage obtained by gas chromatography (hereinafter referred to also as "GC"), unless otherwise specified. The term "production ratio" is a ratio of area percentages obtained by GC.

The term "yield" is calculated from the area percentages obtained by GC.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

The term "crude yield" refers to a yield of a crude product obtained without purification.

In the Examples, monitoring of the reactions and calculation of the yields were carried out in the following GC conditions.
GC conditions: GC: Capillary gas chromatograph GC-2014 (Shimadzu Corporation); column: DB-5, 0.25 mm×0.25 mmφ×30 m; carrier gas: He (1.55 mL/min), detector: FID; column temperature: 100° C., elevated by 5° C./min, up to 230° C.

Synthetic Example 1: Preparation of 2-isopropenyl-5-hexenyl chloride (7: $X^2$=Cl)

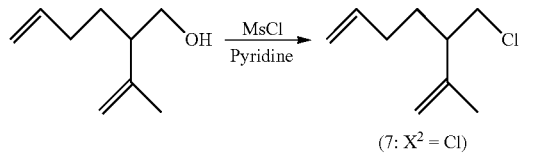

(7: $X^2$ = Cl)

In a reactor were placed 2-isopropenyl-5-hexenol (19.90 g: 0.118 mol), pyridine (22.46 g: 0.284 mol), and dimethylformamide (DMF) (50 ml) in a nitrogen atmosphere and cooled to 5° C. Then, mesyl chloride (MsCl) (22.77 g: 0.199 mol) was added dropwise into the reactor at 10° C. or below over 1 hour. After the completion of the dropwise addition, the mixture was stirred at room temperature (20 to 25° C.) for 1 hour and further at 100 to 110° C. for 6 hours. The mixture was then cooled to 15° C., and pure water (100 g) and hexane (100 g) were added and stirred for 30 minutes. After the completion of the stirring, the organic phase was separated. The separated organic phase was subjected to aftertreatment, i.e., washing, drying, and concentration, to obtain a crude product, 2-isopropenyl-5-hexenyl chloride (7: $X^2$=Cl) (17.00 g). This crude product was subjected to distillation at a reduced pressure to obtain the target compound, 2-isopropenyl-5-hexenyl chloride (7: $X^2$=Cl) (13.53 g: 0.078 mol). A yield from the whole fractions including a first distillation fraction was 71.19%.

The following are spectrum data of the 2-isopropenyl-5-hexenyl chloride (7: $X^2$=Cl) thus prepared.

IR (D-ATR): ν=3077, 2975, 2931, 2859, 1825, 1729, 1642, 1443, 1416, 1377, 1316, 1265, 1168, 994, 898, 744, 637, 562, 546 cm$^{-1}$.

$^1$H-NMR (500 MHz, CDCl$_3$): δ=1.41-1.52 (1H, m), 1.61-1.68 (4H, m), 1.94-2.11 (2H, m), 2.39-2, 44 (1H, m), 3.46-3.53 (2H, m), 4.81 (1H, s-like), 4.92 (1H, s-like), 4.97 (1H, dd-like, J$_1$=10.1 Hz, J$_2$=1.1 Hz), 5.02 (1H, dd-like, J$_1$=17.2 Hz, J$_2$=1.7 Hz), 5.75-5.83 (1H, m) ppm.

$^{13}$C-NMR (125 MHz, CDCl$_3$): δ=18.89, 29.73, 31.14, 47.21, 48.66, 113.79, 114.91, 138.10, 144.00 ppm.

GC-MS (EI, 70 eV): 27, 41, 55, 69, 81, 91, 109, 119, 130, 143, 158.

Example 1: Preparation of 5-isopropenyl-2-methyl-8-nonenyl chloride (4: $X^1$=Cl)

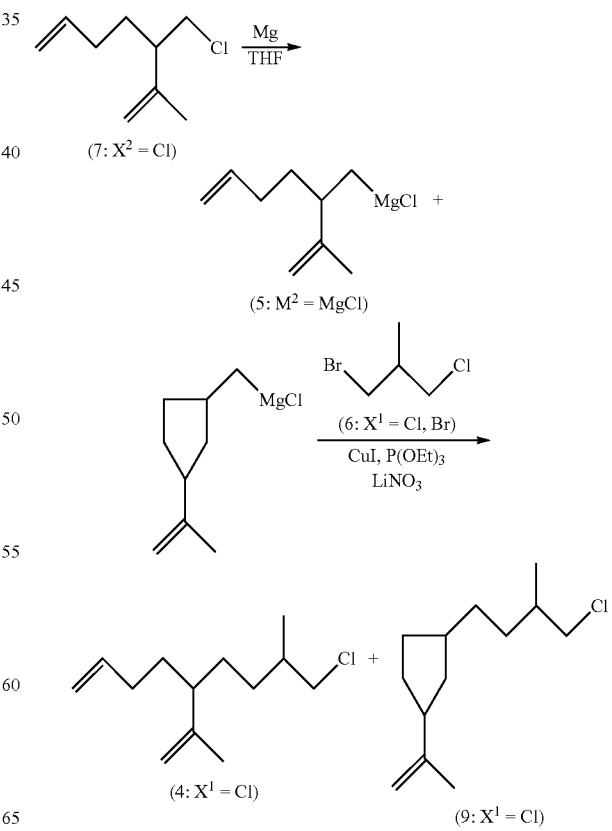

In a reactor were placed magnesium (1.97 g: 0.08 mol) and tetrahydrofuran (THF) (7.6 g) in a nitrogen atmosphere, heated to 60° C., and stirred for 15 minutes. A mixture of 2-isopropenyl-5-hexenyl chloride (7: $X^2$═Cl) prepared in Synthetic Example 1 (12 g: 0.07 mol) and tetrahydrofuran (THF) (15.2 g) was then added dropwise into the reactor over 25 minutes. After the completion of the dropwise addition, the mixture was stirred at an internal temperature of 75 to 80° C. for 2 hours to obtain 2-isopropenyl-5-hexenylmagnesium chloride (5). The obtained 2-isopropenyl-5-hexenylmagnesium chloride (5) was cooled to room temperature.

In another reactor were placed copper(I) iodide (CuI) (0.14 g: 0.0007 mol), lithium nitrate (LiNO$_3$) (0.05 g: 0.0007 mol), triethyl phosphite (P(OEt)$_3$) (0.33 g: 0.002 mol), tetrahydrofuran (THF) (15.2 g), and 1-bromo-3-chloro-2-methylpropane (6: $X^1$═Cl, Br) (13.03 g: 0.08 mol) in a nitrogen atmosphere. The mixture was stirred and cooled to −5° C. to 10° C. The whole amount of the 2-isopropenyl-5-hexenylmagnesium chloride (5) prepared above was then added dropwise into the another reactor at 20° C. or below over 80 minutes. After the completion of the dropwise addition, the mixture was stirred for 1 hour. A mixture of pure water (50 g), ammonium chloride (5 g), and an aqueous 20 wt. % hydrogen chloride solution (1 g) was added into the reactor and stirred for 30 minutes. After the completion of the stirring, the organic phase was separated. The separated organic phase was subjected to aftertreatment, i.e., washing, drying, and concentration, to obtain a crude product, 5-isopropenyl-2-methyl-8-nonenyl chloride (4) (16.27 g: 0.04 mol). The 5-isopropenyl-2-methyl-8-nonenyl chloride (4) had a crude yield of 50.72%. A production ratio of 5-isopropenyl-2-methyl-8-nonenyl chloride (4):cyclic halide compound (9) contained in the crude product was 75:25.

The following are spectrum data of the 5-isopropenyl-2-methyl-8-nonenyl chloride (4: $X^1$═Cl) thus prepared.

IR (D-ATR): ν=3073, 2965, 2930, 2858, 1642, 1441, 1377, 1336, 1294, 994, 910, 891, 731, 687, 641, 579 cm$^{-1}$.

$^1$H-NMR (500 MHz, CDCl$_3$): δ=0.98-1.01 (3H, m), 1.09-1.17 (1H, m), 1.25-1.44 (5H, m), 1.58-1.59 (3H, m), 1.73-1.82 (1H, m), 1.86-2.06 (3H, m), 3.37-3.55 (2H, m), 4.68 (1H, s-like), 4.76 (1H, s-like), 4.91-5.01 (2H, m), 5.75-5.84 (1H, m) ppm.

$^{13}$C-NMR (125 MHz, CDCl$_3$): δ=17.61, 17.66, 17.71, 17.98, 30.40, 30.47, 31.61, 31.73, 32.55, 32.68, 35.55, 46.82, 46.94, 51.00, 51.25, 112.01, 112.11, 114.28, 138.93, 146.78, 146.91 ppm.

GC-MS (EI, 70 eV): 29, 41, 55, 69, 81, 95, 109, 123, 135, 149, 171, 186, 199, 214.

Example 2: Preparation of 6-isopropenyl-3-methyl-9-decenol (2)

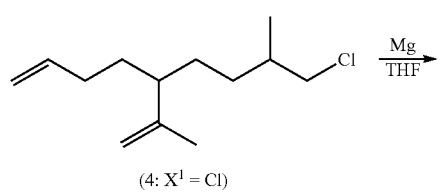

(4: $X^1$ = Cl)

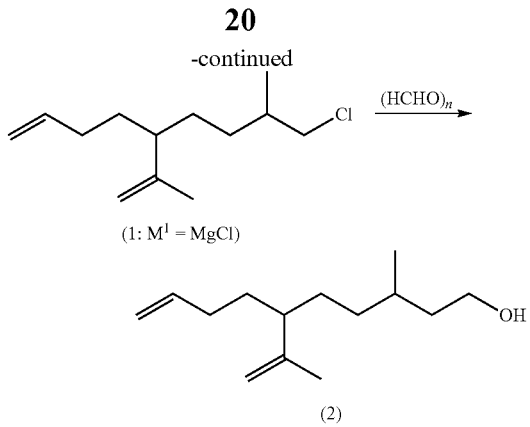

(1: $M^1$ = MgCl)

(2)

In a reactor were placed magnesium (0.70 g: 0.03 mol) and tetrahydrofuran (THF) (2.7 g) in a nitrogen atmosphere, heated to 60° C., and stirred for 15 minutes. A mixture of 1-chloro-5-isopropenyl-2-methyl-8-nonene (4: $X^1$═Cl) (5.83 g: 0.02 mol) and tetrahydrofuran (THF) (5.4 g) was then added dropwise into the reactor over 25 minutes. After the completion of the dropwise addition, the mixture was stirred at an internal temperature of 75 to 80° C. for 2 hours to obtain 5-isopropenyl-2-methyl-8-nonenylmagnesium chloride (1: $M^1$=MgCl).

Then, paraformaldehyde ((HCHO)$_n$) (0.78 g) was added into the reactor over 10 minutes with the internal temperature being kept at 75 to 80° C., and then stirred at 75 to 80° C. for 1 hour. Further, paraformaldehyde (0.5 g) was then added into the reactor at 75 to 80° C. over 10 minutes. After the completion of the dropwise addition, the mixture was stirred at 75 to 80° C. for 1 hour. The mixture was then cooled to room temperature, and an aqueous 20 wt. % hydrogen chloride solution (15 g) was added and stirred for 30 minutes. After the completion of the stirring, the organic phase was separated. The separated organic phase was subjected to aftertreatment, i.e., washing, drying, and concentration, to obtain a crude product, 6-isopropenyl-3-methyl-9-decenol (2) (5.55 g). The crude product had a crude yield of 58.33%.

The following are spectrum data of 6-isopropenyl-3-methyl-9-decenol (2) thus prepared.

IR (D-ATR): ν=3332, 3074, 2928, 2871, 1642, 1452, 1376, 1058, 994, 909, 889, 641 cm$^{-1}$.

$^1$H-NMR (500 MHz, CDCl$_3$): δ=0.87-0.90 (3H, m), 1.00-1.09 (1H, m), 1.17-1.69 (12H, m), 1.87-2.08 (3H, m), 3.60-3.70 (2H, m), 4.66 (1H, s-like), 4.74 (1H, s-like), 4.90-5.02 (2H, m), 5.75-5.84 (1H, m) ppm.

$^{13}$C-NMR (125 MHz, CDCl$_3$): δ=17.63, 17.79, 18.52, 19.77, 29.29, 29.61, 30.46, 30.64, 30.65, 32.56, 32.74, 34.62, 34.88, 39.63, 40.04, 46.91, 47.10, 61.11, 61.14, 111.70, 111.81, 114.17, 139.04, 139.06, 147.21, 147.28 ppm.

GC-MS (EI, 70 eV): 29, 41, 55, 69, 81, 95, 109, 123, 135, 149, 167, 182, 195, 210.

Example 3: Preparation of 6-isopropenyl-3-methyl-9-decenyl acetate (3)

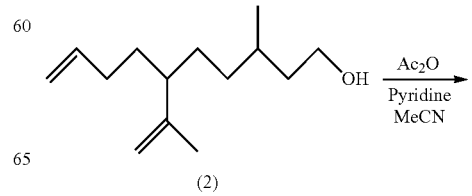

(2)

-continued

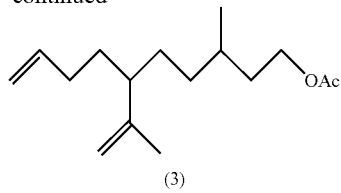

(3)

In a reactor were placed 6-isopropenyl-3-methyl-9-decenol (2) obtained by repeating the procedures of Example 2 (215.33 g: 0.77 mol), pyridine (213.45 g: 2.70 mol), acetic anhydride (131.78 g: 1.29 mol), and acetonitrile (MeCN) (220 g) in a nitrogen atmosphere and stirred at room temperature (20 to 25° C.) for 4 hours 45 minutes. Pure water (600 g) and n-hexane (300 g) were then added into the reactor and stirred for 30 minutes. After the completion of the stirring, the organic phase was separated. The separated organic phase was subjected to aftertreatment, i.e., washing, drying, and concentration, to obtain a crude product, 6-isopropenyl-3-methyl-9-decenyl acetate (3) (245.31 g). This crude product was subjected to distillation at a reduced pressure to obtain the target compound, 6-isopropenyl-3-methyl-9-decenyl acetate (3) (142.32 g: 0.55 mol). A yield from the whole fractions including a first distillation fraction was 83.27%.

The following are spectrum data of 6-isopropenyl-3-methyl-9-decenyl acetate (3) thus prepared.

IR (D-ATR): ν=3073, 2928, 2871, 1742, 1642, 1454, 1367, 1239, 1037, 995, 909, 889, 636, 606 cm$^{-1}$.

$^1$H-NMR (500 MHz, CDCl$_3$): δ=0.87-0.90 (3H, m), 1.01-1.09 (1H, m), 1.18-1.54 (7H, m), 1.56-1.58 (3H, m), 1.59-1.68 (1H, m), 1.89-2.01 (3H, m), 2.02 (3H, s), 4.01-4.12 (2H, m), 4.65 (1H, s-like), 4.74 (1H, s-like), 4.91-5.01 (2H, m), 5.74-5.83 (1H, m) ppm.

$^{13}$C-NMR (125 MHz, CDCl$_3$): δ=17.63, 17.77, 19.32, 19.63, 20.99, 29.68, 29.96, 30.43, 30.56, 31.62, 31.65, 32.56, 32.72, 34.49, 34.64, 35.19, 35.64, 46.89, 47.04, 62.98, 63.02, 111.77, 111.86, 114.19, 138.99, 147.03, 147.15, 171.16 ppm.

GC-MS (EI, 70 eV): 29, 43, 55, 67, 81, 95, 109, 123, 135, 149, 163, 177, 192, 209, 223, 237, 252.

The invention claimed is:
1. A process for preparing a 5-isopropenyl-2-methyl-8-nonenyl halide compound of the following general formula (4):

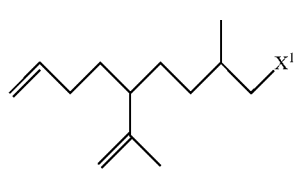

(4)

wherein X$^1$ represents a halogen atom,
the process comprising steps of:
subjecting a nucleophilic reagent, 2-isopropenyl-5-hexenyl compound, of the following general formula (5):

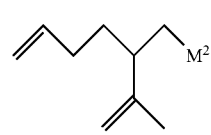

(5)

wherein M$^2$ represents Li, MgZ$^2$, ZnZ$^2$, Cu, CuZ$^2$, or CuLiZ$^2$, wherein Z$^2$ represents a halogen atom or a 2-isopropenyl-5-hexenyl group,
to a coupling reaction with a 1,3-dihalo-2-methylpropane compound of the following general formula (6):

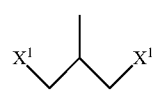

(6)

wherein X$^1$ represents, independently of each other, a halogen atom,
to form 5-isopropenyl-2-methyl-8-nonenyl halide compound (4).

* * * * *

UNITED STATES PATENT AND TRADEMARK OFFICE
CERTIFICATE OF CORRECTION

PATENT NO. : 11,958,801 B2
APPLICATION NO. : 18/154068
DATED : April 16, 2024
INVENTOR(S) : Baba et al.

It is certified that error appears in the above-identified patent and that said Letters Patent is hereby corrected as shown below:

In the Specification

Column 15, Line 13: Please correct "AScetate" to read --Acetate--

Column 20, Lines 1-8: Please delete the formula and replace with the following:

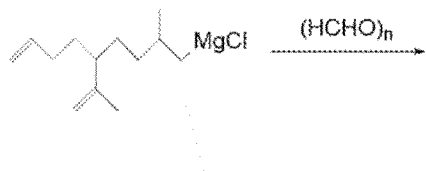

($1: M^1 = MgCl$)

Signed and Sealed this
Eighth Day of April, 2025

Coke Morgan Stewart
*Acting Director of the United States Patent and Trademark Office*